United States Patent
Xu et al.

(10) Patent No.: US 9,290,787 B2
(45) Date of Patent: Mar. 22, 2016

(54) METHOD OF PRODUCING NATURAL β-CAROTENE BY FERMENTATION AND USE THEREOF

(75) Inventors: Xinde Xu, Donglu (CN); Mingqing Jiao, Donglu (CN); Dong Shao, Donglu (CN); Bin Shao, Donglu (CN); Leiming Yu, Donglu (CN)

(73) Assignee: Zhejiang Medicine Co., Ltd., Xinchang Pharmaceutical Factory, Donglu (CN)

( * ) Notice: Subject to any disclaimer, the term of this patent is extended or adjusted under 35 U.S.C. 154(b) by 259 days.

(21) Appl. No.: 14/119,149

(22) PCT Filed: May 15, 2012

(86) PCT No.: PCT/CN2012/000655
§ 371 (c)(1),
(2), (4) Date: Nov. 20, 2013

(87) PCT Pub. No.: WO2012/159446
PCT Pub. Date: Nov. 29, 2012

(65) Prior Publication Data
US 2014/0187829 A1 Jul. 3, 2014

(30) Foreign Application Priority Data
May 20, 2011 (CN) .......................... 2011 1 0132328

(51) Int. Cl.
| | |
|---|---|
| C07C 1/00 | (2006.01) |
| C12P 23/00 | (2006.01) |
| A23L 1/303 | (2006.01) |
| A23L 1/275 | (2006.01) |
| A61K 31/015 | (2006.01) |

(52) U.S. Cl.
CPC ............... *C12P 23/00* (2013.01); *A23L 1/2753* (2013.01); *A23L 1/303* (2013.01); *A61K 31/015* (2013.01); *A23V 2002/00* (2013.01)

(58) Field of Classification Search
CPC .................................... C07C 1/00; C12P 23/00
USPC .............................................. 585/638; 435/67
See application file for complete search history.

(56) References Cited

U.S. PATENT DOCUMENTS 3,579,424 A * 5/1971 Purcell .................... C12P 23/00
252/645

* cited by examiner

*Primary Examiner* — Thuan D Dang
(74) *Attorney, Agent, or Firm* — William D. Hare, Esq.; McNeely Hare & War, LLP

(57) ABSTRACT

The present invention provides a method for producing and purifying β-carotene by *Blakeslea trispora* fermentation and use thereof. The method comprises the following steps: a) separately inoculating the *Blakeslea trispora* strains onto a PDA culture medium so as to obtain a spore suspension; b) propagating spores in a seeding tank so as to obtain seeds for fermentation; c) inoculating the seeds for fermentation onto a fermenter and fermenting said seeds; d) adjusting the fermentation liquid to be basic by using an organic or inorganic base, and filtering so as to obtain wet mycelia; e) treating the wet mycelia with a hydrophobic non-polar organic solvent; f) mixing the wet mycelia with an organic solvent of ester and obtaining a concentrated solution by extracting; g) adding a saturated monohydric alcohol into the concentrated solution, and filtering and crystallizing so as to obtain pure ss-carotene. The content of the ss-carotene in the present invention exceeds 96%, and the yield is above 85%.

18 Claims, No Drawings

METHOD OF PRODUCING NATURAL β-CAROTENE BY FERMENTATION AND USE THEREOF

CROSS REFERENCE TO RELATED APPLICATIONS

This application is a national phase application under 35 USC 371 of PCT/CN2012/000655 filed on May 15, 2012 and published as WO 2012/159446 A1, which claims priority to Chinese patent application No. 201110132328.5 filed on May 20, 2011, the contents of both of which are incorporated herein in their entirety by reference.

FIELD OF THE INVENTION

The present invention relates to methods of producing β-carotene by using microorganism fermentation comprising improvement of fermentation and β-carotene extraction and purification methods, and belongs to fields of biochemical engineering.

BACKGROUND OF THE INVENTION

Carotenoid is a kind of pigment with the largest and widest presences in nature. Carotenoid compounds are widely used for pigmentations of foods, cosmetics and pharmaceuticals, etc. Recently studies have shown that carotenoids have better curative effects on preventing, postponing and curing certain diseases as well as improving immunities.

β-carotene is an important carotenoid, its chemical formula is $C_{40}H_{56}$ and its molecular weight is 536.88, and is formed by bonding the double bonds of four isoprenes, mainly has four forms of all-trans, 9-cis-form, 13-cis-form and 15-cis-form. The molecular structural formula of β-carotene is as follows:

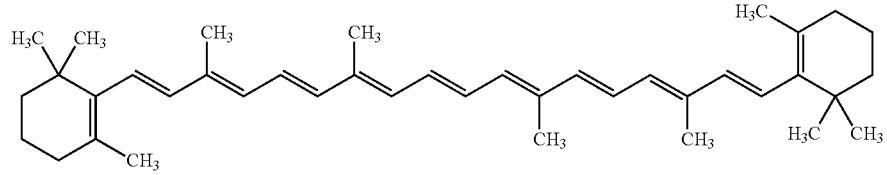 [SMILES: CC1=C(/C=C/C(C)=C/C=C/C(C)=C/C=C/C=C(C)/C=C/C=C(C)/C=C/C2=C(C)CCCC2(C)C)C(C)(C)CCC1]
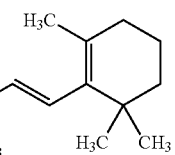

There is a β-ionine ring at each end of molecular structure thereof, the β-ionine could exist in the form of isomer form, substitutional form and opening-ring form.

β-carotene has important physiological functions and may serve as a precursor of vitamin A, and is a nutrition food fortifier with Class A recognized by Joint Expert Committee on Food Additives of United Nations FAO and World Health Organization. Studies have shown that β-carotene as the precursor of vitamin A has effects on antioxidation, influence reproduction and thyroid function etc. Many double bonds in a β-carotene molecule are readily oxidized so as to play a role on antioxidation accordingly and protect bodies from being damaged in the presence of light, heat, oxygen and more activities free radical ions. In addition, studies also have shown that β-carotene can improve immunities, enhance anti-cancer abilities, promote connections and communications between cells, and have anti-nicotine effects and so on.

β-carotene derives from total synthesis and nature. Recently people are in favor of natural β-carotene because β-carotene obtained by total synthesis may exist some chemical intermediate impurities. There are three methods of producing natural β-carotene including extracting from natural plants, culturing salina and producing by microorganism fermentation. A certain amount of natural β-carotene may be obtained by extraction and separation from vegetables containing a trace of β-carotene such as carrot and so on. But deficiencies of the method are obviously a lot of material costs and low production. The second method of obtaining β-carotene is to culture a large area of salina such as *Dunaliella salina* and then solvent extraction. But the culturing salina is strictly restricted by external environmental conditions. It makes production scales difficult to expand and meet market demands. The third method of obtaining β-carotene is to microorganism fermentation. But the method is not restricted by environmental conditions, with high yields and easy to achieve industrialization. More and more research institutes and manufacturers devote themselves to the researches. The microbial strains for producing natural β-carotene at home and abroad are mainly *Bacillus ramosus, Rhodothece glutinis*, etc. Popular strains are filamentous fungus such as *Blakeslea trispora, Neurospora sitophila*, etc., wherein the most popular strain is *Blakeslea trispora*.

Producing natural β-carotene by using *Blakeslea trispora* is to mix and fermente two kinds strains thereof such as strains (+) and (−), The method is in detail described in PCT application of WO 00/77234, Caglioti L. et al. (1966). Recently researches mainly pay attention to how to change fermentation conditions or add precursor substances to increase fermentation unit and how to effectively *separate* and obtain high quality pure β-carotenes from fermented mycelia. More patent documents have reported these aspects and shown many improving measures. But there are many technical deficiencies in these measures or production processes, for example, higher costs of producing due to low fermentation units and then no beneficial for industrial production; or complicated processes of extraction and purification of β-carotene, or difficultly extracted intracellular products in fermentation; or food safety risks due to greater toxicity organic solvents used in extraction and purification; or low content of β-carotene due to more impurities.

U.S. Pat. No. 3,752,740 produces natural β-carotene by using *Blakeslea trispora* fermentation by adding 7.5% citric acid into medium. But the fermentation unit in the final fermentation liquid is too low to be suitable for industrial production.

U.S. Pat. No. 7,252,965 discloses a selected and optimized *Blakeslea trispora*, and increases yields of β-carotene in the fermentation liquid by measures of adding precursor substance β-ionine and increasing dissolved oxygen constrainedly during fermentation courses, and β-carotene unit in the final fermentation liquid can achieve to 9 g/L. The process does not relate to any courses of extracting β-carotene from mycelia.

CN 1,193,048A provides processes of preparing β-carotene by culturing filamentous fungus to ferment in a fermenter. The process comprises Level 1 strain culture and Level 2 strain culture as well as fermentation course. The PDA medium thereof comprises glucose, potato and agar medium. The medium of Level 2 strain culture and fermentation culture comprises starch, glucose, starch, corn syrup, dipotassium hydrogen phosphate, magnesium sulfate, thiamine hydrochloride and vegetable oil, etc. The process improves dissolved oxygen by improvements of equipment, but the fermentation unit is low in the fermentation liquid, and large quantities of greater toxicity organic solvent such as N-hexane, etc. is used in the extraction.

EP 1,306,444 B1 relates to a method of producing β-carotene by using *Blakeslea trispora* to ferment and extracting β-carotene from mycelia. It needs to add lecithin and adjust pH of fermentation liquid stage-by-stage during fermentation process. But there are many steps in the process of extraction and purification of β-carotene, such as refining filtrating mycelia by alcohols, drying and pulverizing mycelia, extracting by organic solvents, concentrating organic solvents after extraction, crystallizing by adding alcohols solvent, filtrating and drying, etc. The processes of extraction and purification of β-carotene are very complicated including drying and pulverizing steps for at least three times, drying and pulverizing wet mycelia after refining, drying and pulverizing pure β-carotene after extraction, and drying the residua of mycelia after the extraction of β-carotene being completed. Likewise, it certainly involves three times transfer processes of powder materials and will bring series of additional requirements for equipments and techniques in the industrial production, and twice heating and drying processes are very bad for unstable substances when β-carotene heated. It certainly makes yields of final product decrease. In addition, pulverizing processes of mycelia increases working procedures. Besides fine powders in the pulverizing process is also bad for occupational health.

In brief, there are such deficiencies as complicated processes and inadequacy for industrial production in the prior art. So it is necessary to find a method of producing β-carotene with high yield via *Blakeslea trispora* and expediently extracting β-carotene produced by fermentation in spores by an effective way. The present invention provides a method of obtaining natural β-carotene with high yields by culturing *Blakeslea trispora*.

SUMMARY OF THE INVENTION

The present invention relates to an improved method of producing β-carotene by using filamentous fungus especially *Blakeslea trispora* and processes of extraction and purification thereof.

In the process of producing β-carotene by fermenting and culturing filamentous fungus especially *Blakeslea trispora*, it often adopts two methods so as to increase β-carotene in the fermentation liquid. One of them is to add precursor into the medium, the other one is to increase a dissolved oxygen as far as possible. It is very necessary and beneficial to increase concentration of oxygen in the medium because producing β-carotene by filamentous fungus is an aerobic fermentation. These measures are usually to change stirring forms of fermenter or accelerate stirring speeds and add oxygen constrainedly. But effects of these measures are not very ideal because these measures not only increase energy consumption but also accelerate stirring speed and then make growing mycelia broken and make biomass decrease and consequently bring about negative impacts.

At present, it has been reported that adding vegetable oils into the medium can increase the fermentation unit of β-carotene. But a question of adding vegetable oils into the medium is not to be well dispersed in water-based medium and then result in low utilization rates of vegetable oils because of vegetable oils fat-soluble. On the other hand, adding a large quantity of vegetable oils will decrease oxygen concentration in the medium and also reduce β-carotene concentrations in the final fermentation liquid. Adding a certain amount of emulsifier into the medium could make vegetable oils well dispersed in the water-based medium, but adding a large quantity of emulsifier produces more foams in the fermentation and then makes operation inconvenient.

The present invention finds out a convenient method of making vegetable oils in the water-based medium well dispersed and at the same time can increase oxygen concentration in the medium.

The present invention provides a method of producing and purifying β-carotene by fermentations of *Blakeslea trispora*, the method comprises the following steps:

a) inoculating strains of *Blakeslea trispora* "+" and "−" into a PDA medium, culturing at 25-30° C. for 48-60 hours, eluting spores with a sterile saline to a spore suspension after growth of a great deal of spores; wherein the strains of *Blakeslea trispora* "+" and "−" are purchased from ATCC 14271 (+) and ATCC 14272 (−).

b) culturing and propagating spores of the fresh spore suspension in a seeding tank at pH=6.3~6.8 and the cultivation temperature of 25-30° C. to seeds for fermentation, wherein a seed medium comprises corn starch, glucose, vegetable oil, thiamine hydrochloride, magnesium sulfate and emulsifier;

c) inoculating the seeds for fermentation in the seeding tank of step b) into a fermentation liquid at pH=6.5~6.8 and temperature of 27-30° C.; wherein the medium is high-speed sheared and emulsified by a colloidal mill before inoculating, the medium of fermenter comprises corn starch, corn syrup, meal bread flour, vegetable oil, dipotassium hydrogen phosphate, magnesium sulfate, thiamine hydrochloride, and/or emulsifier;

d) adjusting the fermentation liquid of step c) to pH=8.0~8.5 by organic base or inorganic base, and then filtrating so as to obtain a wet mycelia;

e) treating the wet mycelia of step d) by hydrophobic non-polar organic solvents at 0° C.~60° C., extracting and continuously filtering so as to obtain a wet mycelia without fat-soluble impurities;

f) mixing the wet mycelia of step e) using organic solvent of esters at temperature of 10° C. up to a boiling point of solvent, extracting and concentrating to dryness in vacuum at temperature ≤40° C. so as to obtain a concentrated solution; and g) adding a C1~C6 saturated monohydric alcohol to the concentrated solution at 10° C.~80° C., precipitating crystals and filtering so as to obtain a pure β-carotene.

According to the present invention, more specifically, a certain amount of vegetable oils is added to a medium containing carbon sources, nitrogen sources, phosphorus sources and microelements, with or without emulsifier, the oil droplets can be uniformly dispersed in a water-based medium by high-speed shearing and emulsifying in a colloidal mill, so in subsequent cultivation processes, it not only expands contact opportunities between mildews and vegetable oils, tiny vegetable oil droplets can be fully utilized by microorganism, thereby increases yields of β-carotene. Moreover, a great deal of oxygen is immersed into the medium during high-speed shearing and consequently increase oxygen concentrations in the medium and is also beneficial for subsequent cultivation processes.

The vegetable oil in the medium can be added in one time or in batches. On the one hand, it is unnecessary to use high concentrations of vegetable oils in early fermentation, because the vegetable oil cannot be fully utilized. On the other hand, excessive vegetable oils will make viscosity of medium higher, and consequently is not beneficial for oxygen dissolved, Adding vegetable oils in batches, for example, adding a certain amount of vegetable oils in early stage and then, supplementing remaining vegetable oils after vegetable oils consumed in the fermentation process, not only makes viscosity of medium relatively homogeneous, but also makes full uses of vegetable oils in order to increase utilization rates of raw materials.

The carbon sources in the medium may be one or more carbohydrates or fatty substances such as glucose, sucrose, starch, vegetable oil or animal oil. The nitrogen source may be one or more organic or inorganic nitrogen sources such as soy protein, corn protein, yeast extract, peptides, casein, etc. A certain amount of microelement such as phosphate, sulfate, calcium salt, magnesium salt, etc. may be added into the medium. Specifically proportions and concentrations of carbon sources, nitrogen sources, phosphorus sources and microelements are beneficial for growth of microorganisms and improvement of fermentation units.

In the step c), the vegetable oil in the medium is added in batches or in one-time, the added amount of the vegetable oil is 1-10% of the total mass of medium, preferably 3-6%. In the step c), the added amount of vegetable oil is 10-90% of the total mass thereof before shearing, emulsifying and mixing, preferably 40-70%. The emulsifier may be general emulsifiers such as Tween series products, Span series products and lecithin, mono- and di-glycerides, etc. In the steps b) and c), the added mass of the emulsifier is 0.01-10.0% of a volume amount of medium, preferably 0.1-5.0%, more preferably 0.5-2.0%.

Preferably, the vegetable oil is one or more kinds selected from the group consisting of soybean oil, sunflower oil, rapeseed oil, cottonseed oil. The emulsifier is Tween series products, Span series products, lecithin, or mono- and di-glycerides.

Preferably, the seed medium in the step b) comprises (per liter): 20 g~24 g of corn starch, 11 g~17 g of glucose, 10 g~100 g of vegetable oil, 0.02 g of thiamine hydrochloride, 0.3 g of magnesium sulfate, 0.1 g~100.0 g of emulsifier.

Preferably, the medium of the fermenter in the step c) comprises (per liter): 19 g~25 g of corn starch, 17 g~31 g of corn syrup, 12 g~19 g of meal bread flour, 10 g~50 g of vegetable oil, 2 g of dipotassium hydrogen phosphate, 0.3 g~0.4 g of magnesium sulfate and 0.02 g thiamine hydrochloride, and/or 1.0 g~50.0 g of emulsifier.

Preferably, the inorganic base is sodium hydroxide or potassium hydroxide, and the organic base is sodium methoxide or sodium ethoxide in the step d). After fermentation, the fermentation liquid is adjusted to be alkaline by adding organic base or inorganic base such as sodium hydroxide or potassium hydroxide or sodium methoxide or sodium ethoxide, etc. to make pH of the fermentation liquid to be pH=8.0, and make the cell wall broken after maintaining 0.1-2.0 hours.

The wet mycelia are extracted by conventional methods such as filtrating, filter-pressing, centrifugating and the like.

The fat-soluble impurities in the mycelia are removed by treating the wet mycelia with cold non-polar organic solvent. A great deal of vegetable oils are used in the fermentation process. On the one hand, a small part of these vegetable oils may not be completely used by microorganism, on the other hand, more fat-soluble substances will be produced by microorganism in the metabolism, the presence of these fat-soluble substances brings bad impacts on extraction yield and purification for subsequent productions. So it should be removed as much as possible in early stage. The solubility of β-carotene produced by fermentation is very low in non-polar organic solvents. Especially, the solubility is lower when the temperature is lower. The fat-soluble organic impurities can be removed by adding non-polar organic solvent at lower temperature in the case of no loss of β-carotene, and then create conditions for subsequent extraction and purification of β-carotene.

Preferably, the wet mycelia and the hydrophobic non-polar organic solvent are thoroughly mixed in the step e), the volume ratio of the hydrophobic non-polar organic solvent with wet mycelia is 0.5/1-10/1 (V/V), preferably 1/1-5/1 (V/V). The wet mycelia are treated by the hydrophobic non-polar organic solvent at 0-60° C. in the step e), preferably at 10-40° C. The time of treating wet mycelia by the hydrophobic non-polar organic solvent is 0.1-3.0 hr, preferably 0.5-2.0 hr in the step e). The hydrophobic non-polar organic solvent is n-hexane, cyclohexane, or n-heptane in the step e). The wet mycelia without fat-soluble impurities is obtained by filtration after treating the wet mycelia.

β-carotene in wet mycelia is extracted by organic solvent after fat-soluble organic impurities are removed in the step f). The organic solvent is mainly ester organic solvent, the ester organic solvent is ethyl acetate, isopropyl acetate, isobutyl acetate, or butyl acetate. Mixing and extracting at the temperature from 10° C. to the boiling point of solvent, preferably 30° C.~60° C. in order to reduce the β-carotene losses during extraction process. The ratio of the solvent in extraction is determined by the unit in the mycelia, generally, the volume amount of the organic solvent of esters is 5-30 times of the mass of wet mycelia in the step f), preferably 10-20 times.

The organic solvent after extraction is concentrated in the step g). The pure product can be obtained by adding alcoholic organic solvents to crystallize after the solvent is concentrated or directly filter partial crystals precipitated in the concentration process, a remaining part of the crystals is precipitated and crystallized by adding alcohols organic solvent after concentrating the solvent to dryness. C1~C6 saturated monohydric alcohol is ethanol, isopropanol, propylene glycol, or n-propanol. C1~C6 saturated monohydric alcohol is 5-50 times the volume of concentrated solution, preferably 10-30 times. C1~C6 saturated monohydric alcohol is added to the concentrated solution at 10-80° C., preferably at 30-60° C. A pure β-carotene is obtained by drying the crystals, the content thereof is more than 96%, the extraction yield can achieve to about 85%.

In the present invention, β-carotene unit in the final fermentation liquid can reach to 11 g/l at most by changing the medium composition and adding method and making a cultivation liquid through a special emulsification treatment. The cell wall is broken by adjusting pH of the fermentation liquid after completion of the fermentation, the generic lipophilic components are removed by cold non-polar organic solvents, β-carotene in the cell is extracted by edible organic solvents, high purity β-carotene crystals can be obtained by crystallization after concentration, wherein the content of β-carotene is more than 96%, the extraction yield is about 85%. In the entire production process, the operation is simple, the loss of β-carotene is low, and the yield is high, and then the method is applicable for industrial production. The present invention relates to a method of producing natural β-carotene with higher yield by microorganism fermentation, extraction and purification. The content of final obtained natural β-carotene can achieve to up to 96%.

The present invention also provides uses of β-carotene prepared by above mentioned method in the preparation of food additives, dietary supplements, pharmaceuticals or cosmetics. β-carotene crystals can be prepared for microcapsule formulation products by applications of microencapsulation technology. The product has good stability and can be directly applied or be prepared for oil suspension products that can be dispersed in oils.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

The strains of Blakeslea trispora "+" and "−" having deposited and capable of metabolizing β-carotene are separately inoculated into a PDA medium (potato dextrose agar medium), wherein the strains of Blakeslea trispora "+" and "−" are purchased from ATCC14271 (+) and ATCC14272 (−) respectively, and then culture at 25° C. for 48 hr, elute spores to a spore suspension by sterile saline after growth of a great deal of spores. The content of spores in the spore suspension is about $1-3 \times 10^6$ cells/ml. The PDA medium comprises glucose, potato and agar mediums.

Spores in the fresh spore suspension are cultured and propagated in a seeding tank to a great deal of mycelia as seeds for fermentation, wherein a seed medium comprises (per liter) 21 g of corn starch, 13 g of glucose, 100 g of peanut oil, 0.02 g of thiamine hydrochloride, 0.3 g of magnesium sulfate, 0.1 g of Tween-20; pH=6.3, the cultivation temperature is 25° C., the cultivation time is 24 hr.

The spores in the seeding tank is inoculated into a fermenter to produce β-carotene by fermentation and culture. The medium of the fermenter comprises (per liter) 23 g of corn starch, 31 g of corn syrup, 12 g of meal bread flour, 30 g of soybean oil, 2 g of dipotassium hydrogen phosphate, 0.3 g of magnesium sulfate, 0.02 g thiamine hydrochloride, 1.0 g of lecithin; pH=6.8. The medium is high-speed sheared and emulsified by a colloidal mill to make the vegetable oil be well dispersed in it, and bring into a great deal of oxygen. The cultivation temperature is 27° C., a soybean oil is supplemented after culturing 24 hr, the amount is 3.3 g per liter of medium. The fermentation is completed after 96 hr. The unit of β-carotene in the fermentation liquid can achieve to 9.65 g/l after completions of fermentation.

NaOH is added to the fermentation liquid to adjust pH=8.0 of the solution, the wet mycelia is obtained by filtration after stirring for 2.0 hr.

The wet mycelia and N-hexane are mixed and stirred at 0° C. The volume of n-hexane is double of the mass of the wet mycelia, the extracting time of mycelium is 3.0 hr. The wet mycelia without fat-soluble impurities is obtained after filtering.

The wet mycelia and 10 times of butyl acetate are fully mixed at 60° C. The extracting solution is obtained by filtering, concentrating to dryness in vacuum, the temperature is no more than 40° C. during concentration.

N-propanol is added to crystallize at 60° C., the adding amount of n-propanol is 10 times of the volume of concentrated solution. Filtering and crystallizing, so as to obtain pure β-carotene. The content thereof reaches to 98.2%, the extraction yield reaches to 82.0%.

The other auxiliary materials such as gelatin, starch, sucrose, vegetable oil, etc., can be added to the β-carotene crystals as food additives or pharmaceuticals.

Comparative Example 1-1

The cultivation of Blakeslea trispora spore suspension and seeds as well as cultivation conditions of fermenter in the Comparative Example 1-1 are the same as that of the Example 1. The medium composition in the Comparative Example 1-1 is the same as that of the Example. The difference between the Comparative Example 1-1 and the Example 1 is that the fermentation medium is mixed without processing a colloidal mill at high-speed, and without supplementing vegetable oils in late stage of fermentation. The unit of β-carotene in fermentation liquid is only 5.71 g/l after completion of fermentation.

Example 2

The strains of Blakeslea trispora "+" and "−" having deposited and capable of metabolizing β-carotene are separately inoculated into a PDA medium (potato dextrose agar medium), wherein the strains of Blakeslea trispora "+" and "−" are purchased from ATCC14271 (+) and ATCC14272 (−) respectively, and then culture at 30° C. for 60 hr, elute spores to a spore suspension by sterile saline after growth of a great deal of spores. The content of spores in the spore suspension is about $1-3 \times 10^6$ cells/ml. The PDA medium comprises glucose, potato and agar mediums.

Spores in the fresh spore suspension are germinated and breeded in a seeding tank to a great deal of mycelia as seeds for fermentation, wherein a seed medium comprises (per liter) 24 g of corn starch, 15 g of glucose, 60 g of cottonseed oil, 0.02 g of thiamine hydrochloride, 0.3 g of magnesium sulfate, 5.0 g of Span-40; pH=6.5, the cultivation temperature is 30° C., the cultivation time is 30 hr.

The spores in the seeding tank are inoculated into a fermenter to produce β-carotene by fermentation and culture. The medium of the fermenter comprises (per liter) 25 g of corn starch, 24 g of corn syrup, 15 g of meal bread flour, 10 g of soybean oil, 2 g of dipotassium hydrogen phosphate, 0.4 g of magnesium sulfate, 0.02 g thiamine hydrochloride, 20.0 g of Twain-40; pH=6.5. The medium is high-speed sheared and emulsified by colloidal mill to make the vegetable oil be well dispersed in it, and bring into a great deal of oxygen. The cultivation temperature is 30° C., a soybean oil is supplemented after culturing 24 hr, the amount is 90.0 g per liter of medium. The fermentation is completed after 100 hr. The unit of β-carotene in the fermentation liquid can achieve to 10.78 g/l after completions of fermentation.

KOH is added to the fermentation liquid to adjust pH=8.0 of the solution. The wet mycelia is obtained by filtration after stirring for 2.0 hr.

The wet mycelia and n-heptane are mixed and stirred at 60° C. The volume of n-heptane is double of the mass of the wet mycelia, the extracting time of mycelium is 2.0 hr. The wet mycelia without fat-soluble impurities is obtained after filtering.

The wet mycelia and 30 times of isopropyl acetate are fully mixed at 10° C. The extracting solution is obtained by filtering, concentrating to dryness in vacuum. The temperature is no more than 40° C. during the concentration.

Propylene glycol is added to crystallize at 80° C. The adding amount of propylene glycol is 30 times of the volume of concentrated solution. Filtering and crystallizing, so as to obtain the pure β-carotene. The content thereof reaches to 96.4%, the extraction yield reaches to 81.2%.

The other auxiliary materials such as gelatin, starch, sucrose, vegetable oil, etc., can be added to the β-carotene crystal as food additives or pharmaceuticals.

Example 3

The strains of *Blakeslea trispora* "+" and "−" having deposited and capable of metabolizing β-carotene are separately inoculated into a PDA medium (potato dextrose agar medium), wherein the strains of *Blakeslea trispora* "+" and "−" are purchased from ATCC14271 (+) and ATCC14272 (−) respectively, and then culture at 27° C. for 50 hr, elute spores to a spore suspension by sterile saline after growth of a great deal of spores. The content of spores in the spore suspension is about $1\text{-}3\times10^6$ cells/ml. The PDA medium comprises dextrose, potato and agar mediums.

Spores in the fresh spore suspension are germinated and breeded in a seeding tank to a great deal of mycelia as seeds for fermentation, wherein a seed medium comprises (per liter) 21 g of corn starch, 13 g of glucose, 100 g of peanut oil, 0.02 g of thiamine hydrochloride, 0.3 g of magnesium sulfate, 0.1 g of Tween-20; 22 g of corn starch, 11 g of dextrose, 10 g of soybean oil, 0.02 g of thiamine hydrochloride, 0.3 g of magnesium sulfate, 100 g of mono- and biglyceride; pH=6.5, the cultivation temperature is 27° C., the cultivation time is 26 hr.

The spores in the seeding tank are inoculated into a fermenter to produce β-carotene by fermentation and culture. The medium of the fermenter comprises (per liter) 19 g of corn starch, 27 g of corn syrup, 18 g of meal bread flour, 50 g of rapeseed oil, 2 g of dipotassium hydrogen phosphate, 0.4 g of magnesium sulfate, 0.02 g thiamine hydrochloride, 50.0 g of Tween-60; pH=6.5. The medium is high-speed sheared and emulsified by colloidal mill to make the vegetable oil be well dispersed in it, and bring into a great deal of oxygen. The cultivation temperature is 28° C., a rapeseed oil is supplemented after culturing 24 hr, the amount is 21.5 g per liter of medium. The fermentation is completed after 124 hr. The unit of β-carotene in the fermentation liquid can achieve to 10.24 g/l after completions of fermentation.

Sodium methoxide is added to the fermentation liquid to adjust pH=8.1 of the solution, the wet mycelia is obtained by filtration after stirring for 1.0 hr.

The wet mycelia and cyclohexane are mixed and stirred at 40° C. The volume of cyclohexane is 10.0 times of the mass of the wet mycelia, the extracting time of mycelium is 0.1 hr. The wet mycelia without fat-soluble impurities is obtained after continuous filter-pressing.

The wet mycelia and 20 times of isobutyl acetate are fully mixed at 50° C. The extracting solution is obtained by filtering, concentrating to dryness in vacuum. The temperature is no more than 40° C. during the concentration.

Isopropanol is added to crystallize at 10° C. The adding amount of isopropanol is 50 times of the volume of concentrated solution. Filtering and crystallizing, so as to obtain the pure β-carotene. The content thereof reaches to 97.1%, the extraction yield reaches to 86.1%.

The other auxiliary materials such as gelatin, starch, sucrose, vegetable oil, etc., can be added to the β-carotene crystal as food additives or pharmaceuticals.

Example 4

The strains of *Blakeslea trispora* "+" and "−" having deposited and capable of metabolizing β-carotene are separately inoculated into a PDA medium (potato dextrose agar medium), wherein the strains of *Blakeslea trispora* "+" and "−" are purchased from ATCC14271 (+) and ATCC14272 (−) respectively, and then culture at 28° C. for 55 hr, elute spores to a spore suspension by sterile saline after growth of a great deal of spores. The content of spores in the spore suspension is about $1\text{-}3\times10^6$ cells/ml. The PDA medium comprises dextrose, potato and agar mediums.

Spores in the fresh spore suspension are germinated and breeded in a seeding tank to a great deal of mycelia as seeds for fermentation, wherein a seed medium comprises (per liter) 20 g of corn starch, 17 g of dextrose, 10 g of sunflower seed oil, 0.02 g of thiamine hydrochloride, 0.3 g of magnesium sulfate, 5.0 g of Span-60; pH=6.8, the cultivation temperature is 29° C., the cultivation time is 28 hr.

The spores in the seeding tank are inoculated into a fermenter to produce β-carotene by fermentation and culture. The medium of the fermenter comprises (per liter) 25 g of corn starch, 17 g of corn syrup, 19 g of meal bread flour, 40 g of rapeseed oil, 2 g of dipotassium hydrogen phosphate, 0.4 g of magnesium sulfate, 0.02 g thiamine hydrochloride; pH=6.5. The medium is high-speed sheared and emulsified by colloidal mill to make the vegetable oil be well dispersed in it, and bring into a great deal of oxygen. The cultivation temperature is 29° C., a rapeseed oil is supplemented after culturing 24 hr, the amount is 60 g per liter of medium. The fermentation is completed after 124 hr. The unit of β-carotene in the fermentation liquid can achieve to 9.32 g/l after completions of fermentation.

Sodium ethylate is added to the fermentation liquid to adjust pH=8.5 of the solution, the wet mycelia is obtained by filtration after stirring for 1.0 hr.

The wet mycelia and n-hexane are mixed and stirred at 10° C. The volume of n-hexane is 5.0 times of the mass of the wet mycelia. The extracting time of mycelium is 0.5 hr. The wet mycelia without fat-soluble impurities is obtained after filtering.

The wet mycelia and 5 times of ethyl acetate are fully mixed at the boiling point thereof. The extracting solution is obtained by filtering, concentrating to dryness in vacuum, the temperature is no more than 40° C. during concentration. The precipitated partial β-carotene crystals are removed in the concentration process, and continuously concentrate to dryness.

Ethanol is added to crystallize at 30° C. The adding amount of ethanol is 5 times of the volume of concentrated solution. Filtering and crystallizing, so as to obtain the pure β-carotene. The content thereof reaches to 96.1%, the extraction yield reaches to 84.2%.

The β-carotene crystals are grinded and then mixed with safflower oil to produce an oil suspension wherein the content of β-carotene is 30% in the oil suspension. The oil suspension can be prepared to soft capsule for dietary supplement.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A method of producing and purifying β-carotene by *Blakeslea trispora* fermentation, comprising the following steps:
   a) separately inoculating strains of *Blakeslea trispora* "+" and "−" onto a PDA culture medium, culturing at 25-30° C. for 48-60 hours, and then eluting spores to a spore suspension by a sterile saline after growth of a great deal of spores;
   b) culturing and propagating spores of the fresh spore suspension in a seeding tank at pH=6.3~6.8 and the cultivation temperature of 25-30° C. to seeds for fermentation, wherein the seed medium comprises corn starch, dextrose, vegetable oil, thiamine hydrochloride, magnesium sulfate and emulsifier;
   c) inoculating the seeds for fermentation in the seeding tank of step b) onto a fermenter and then fermenting so as to produce a fermentation liquid at pH=6.5~6.8 and the cultivation temperature of 27-30° C.; wherein the medium is high-speed sheared and emulsified by a colloidal mill before inoculating, the medium of the fermenter comprises corn starch, corn syrup, meal bread flour, vegetable oil, dipotassium hydrogen phosphate, magnesium sulfate, thiamine hydrochloride, and/or emulsifier;
   d) adjusting the fermentation liquid of step c) to be pH=8.0~8.5 by using an organic or inorganic base, and then filtrating so as to obtain wet mycelia;
   e) treating the wet mycelia of step d) with hydrophobic non-polar organic solvent at 0° C.~60° C., extracting and continuously filtering so as to obtain a wet mycelia without fat-soluble impurities;
   f) mixing the wet mycelia of step e) with an organic solvent of esters at the temperature from 10° C. to a boiling point of the solvent, and then concentrating to dryness in vacuum at the temperature ≤40° C. to obtain a concentrated solution; and
   g) adding a C1~C6 saturated monohydric alcohol to the concentrated solution at 10° C.~80° C., filtering and crystallizing so as to obtain pure β-carotene.

2. A method according to claim 1, wherein the vegetable oil can be added in one time or in batches, and the added amount of the vegetable oil is 1-10% of the total mass of the medium in step c).

3. A method according to claim 1, wherein the added amount of vegetable oil is 10-90% of the total mass thereof before shearing, emulsifying and mixing in step c).

4. A method according to claim 1, wherein the vegetable oil is one or more kinds selected from the group consisting of soybean oil, sunflower oil, rapeseed oil and cottonseed oil.

5. A method according to claim 1, wherein the added mass of the emulsifier is 0.01-10.0% of a volume amount of the medium in steps b) and c).

6. A method according to claim 1, wherein the emulsifier is polysorbate, sorbitan oleate, lecithin, or mono- and di-glycerides.

7. A method according to claim 1, wherein the inorganic base is sodium hydroxide or potassium hydroxide, the organic base is sodium methoxide or sodium ethoxide in step d).

8. A method according to claim 1, wherein the volume ratio of the hydrophobic non-polar organic solvent with wet mycelia is 0.5/1-10/1 (V/V) in step e).

9. A method according to claim 8, wherein the wet mycelia is treated with the hydrophobic non-polar organic solvent at 10-40° C. in step e).

10. A method according to claim 9, wherein the time of treating the wet mycelia by the hydrophobic non-polar organic solvent is 0.1-3.0 hr in step e).

11. A method according to claim 10, wherein the hydrophobic non-polar organic solvent is n-hexane, cyclohexane, or n-heptane in step e).

12. A method according to claim 1, wherein the volume amount of the organic solvent of esters is 5-30 times of the mass of the wet mycelia in step f).

13. A method according to claim 12, wherein the organic solvent of esters is ethyl acetate, isopropyl acetate, isobutyl acetate, or butyl acetate in step f).

14. A method according to claim 13, wherein the mixing and extracting are at 30-60° C. in step f).

15. A method according to claim 1, wherein the volume of C1~C6 saturated monohydric alcohol is 5-50 times the concentrated solution in step g).

16. A method according to claim 15, wherein the C1~C6 saturated monohydric alcohol is ethanol, isopropanol, propylene glycol or n-propanol in step g).

17. A method according to claim 16, wherein the C1~C6 saturated monohydric alcohol is added to the concentrated solution at 30° C.-60° C. in step g).

18. A method according to claim 1, further comprising incorporating the crystallized β-carotene in one or more of food additives, dietary supplements, pharmaceuticals or cosmetics.

* * * * *